United States Patent
Bertling

(12) 
(10) Patent No.: US 6,468,752 B1
(45) Date of Patent: Oct. 22, 2002

(54) AGENT AND METHOD FOR DETECTING CHEMICAL SUBSTANCES

(75) Inventor: Wolf Bertling, Erlangen (DE)

(73) Assignee: november Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/623,581

(22) PCT Filed: Mar. 2, 1999

(86) PCT No.: PCT/DE99/00558

§ 371 (c)(1),
(2), (4) Date: Nov. 13, 2000

(87) PCT Pub. No.: WO99/45142

PCT Pub. Date: Sep. 10, 1999

(30) Foreign Application Priority Data

Mar. 3, 1998 (DE) .......................... 198 08 884

(51) Int. Cl.[7] .................................. C12Q 1/68
(52) U.S. Cl. .................... 435/6; 435/91.1; 435/91.2; 435/5; 536/24.3; 935/77; 935/78
(58) Field of Search .................. 435/6, 91.1, 91.2, 435/5; 536/24.3; 935/77, 78

(56) References Cited

U.S. PATENT DOCUMENTS

| | | | |
|---|---|---|---|
| 5,156,972 A | | 10/1992 | Issachar |
| 5,607,834 A | | 3/1997 | Bagwell |
| 5,665,558 A | * | 9/1997 | Frame et al. .............. 435/7.25 |
| 5,759,820 A | * | 6/1998 | Hornes et al. ............. 435/91.1 |
| 5,770,365 A | * | 6/1998 | Lane et al. ..................... 435/6 |

FOREIGN PATENT DOCUMENTS

| | | |
|---|---|---|
| EP | 0745690 | 12/1996 |
| EP | 0762122 | 3/1997 |
| WO | WO 97/09342 | 3/1997 |
| WO | WO 98/51819 | 11/1998 |

OTHER PUBLICATIONS

Holme & Peck, Analytical Biochem., 1983, Longman Inc., New York, pp. 243–244.

* cited by examiner

*Primary Examiner*—W. Gary Jones
*Assistant Examiner*—Janell E. Taylor
(74) *Attorney, Agent, or Firm*—Fish & Richardson, P.C., P.A.

(57) ABSTRACT

The invention relates to an agent for detecting chemical substances, comprising: a first polynucleotide or peptide sequence having a first fluorophore molecule, the first end of said sequence being bonded on a solid phase and a second polynucleotide or peptide sequence having a second fluorophore molecule, the second end of said sequence having a group that is sensitive to the chemical substance to be detected. The first polynucleotide or peptide sequence can be hybridized to the second polynucleotide or peptide sequence in such a way that a spatial relationship enabling an interaction betweeen the first and the second fluorophore molecule is produced. When the chemical substance including a physical property is attached to the group and the influence of an external force is exerted on the physical property, the spatial relation can be eliminated, thereby generating or abolishing a fluorescent reaction.

21 Claims, 4 Drawing Sheets

Figure 1:
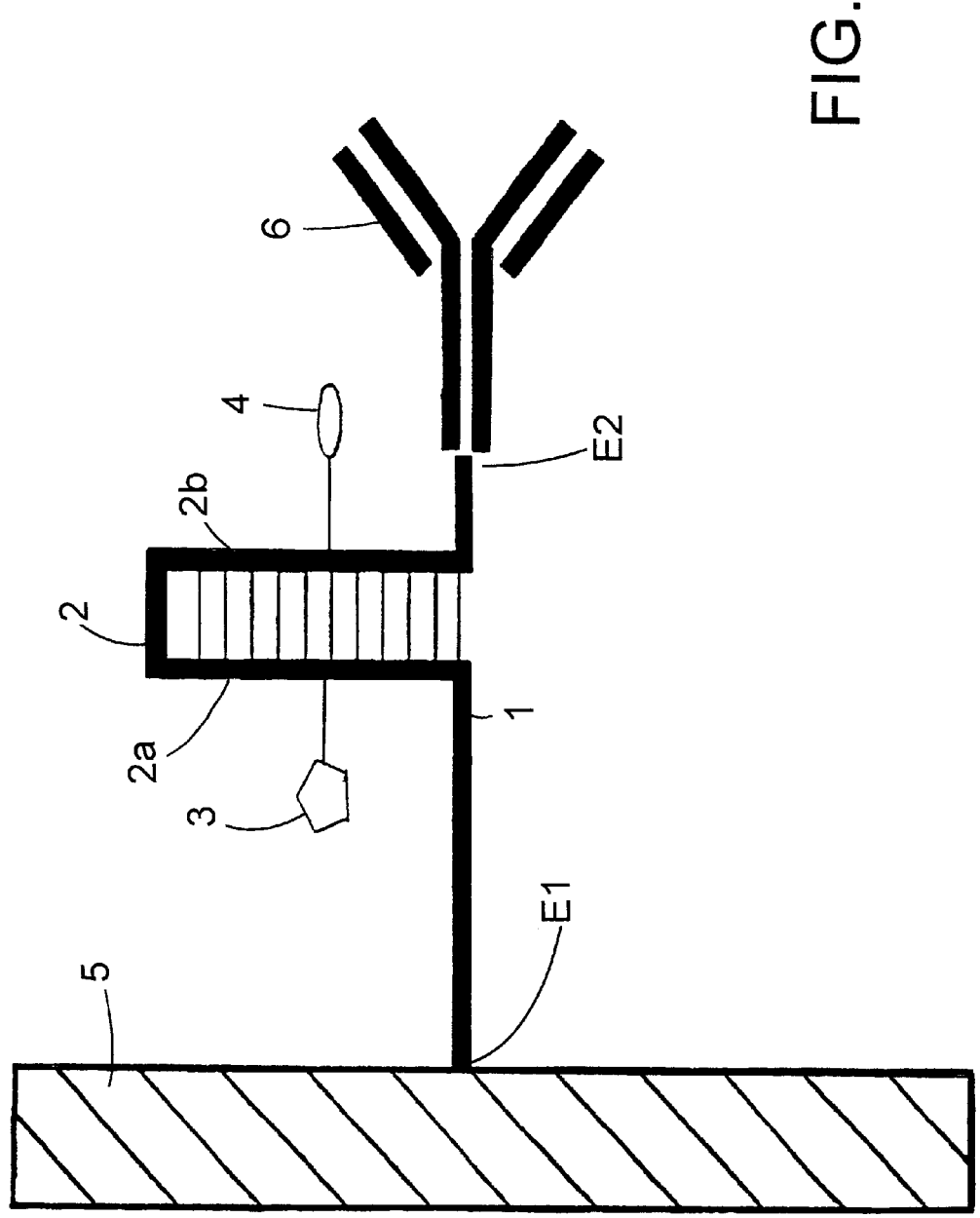

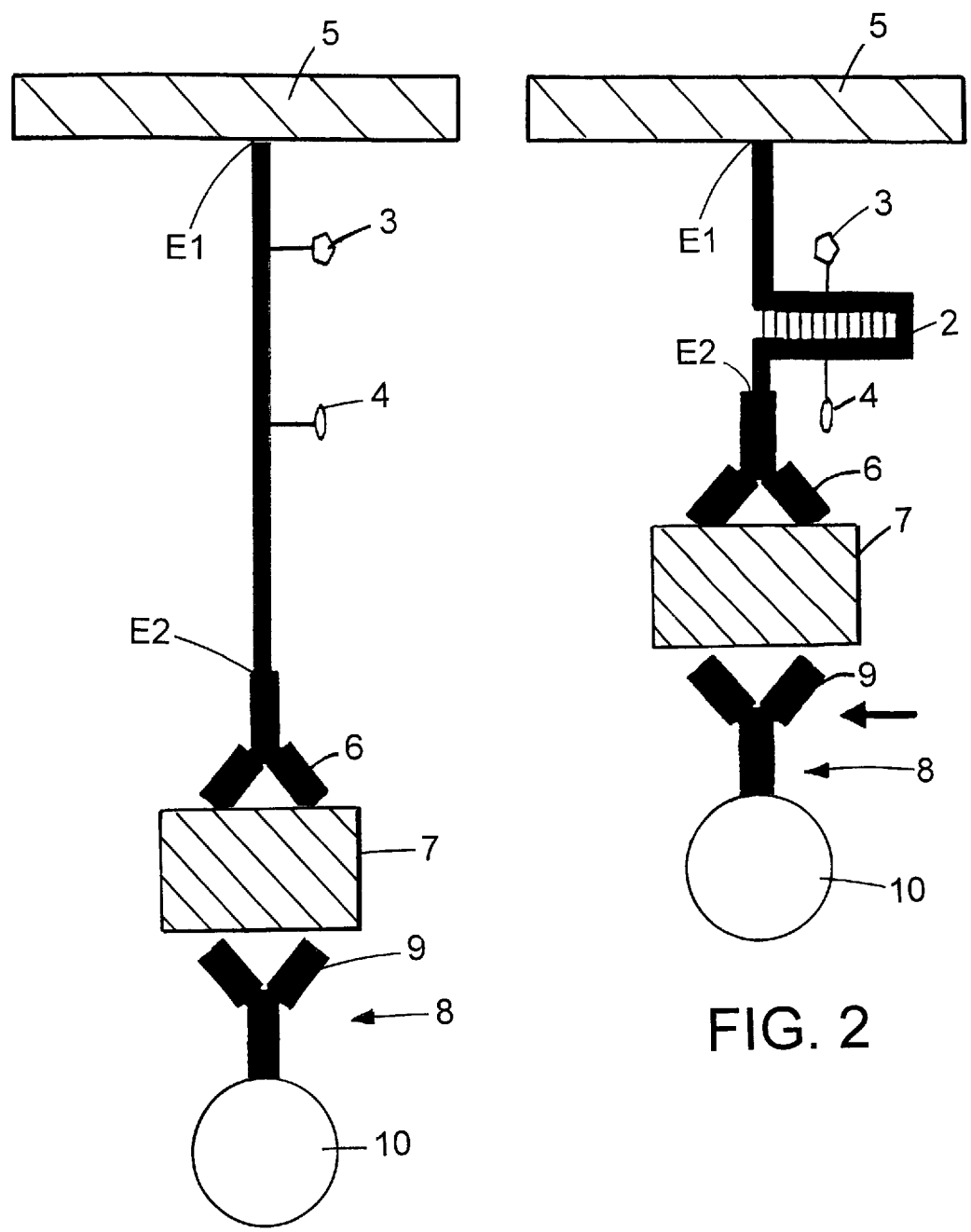
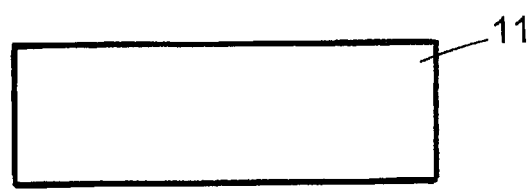

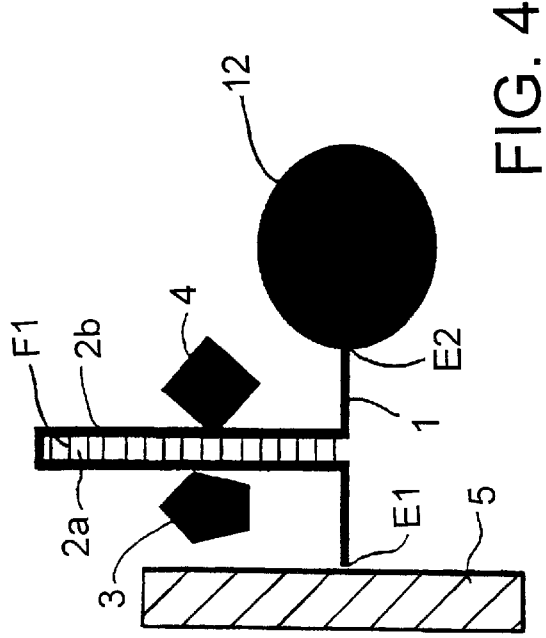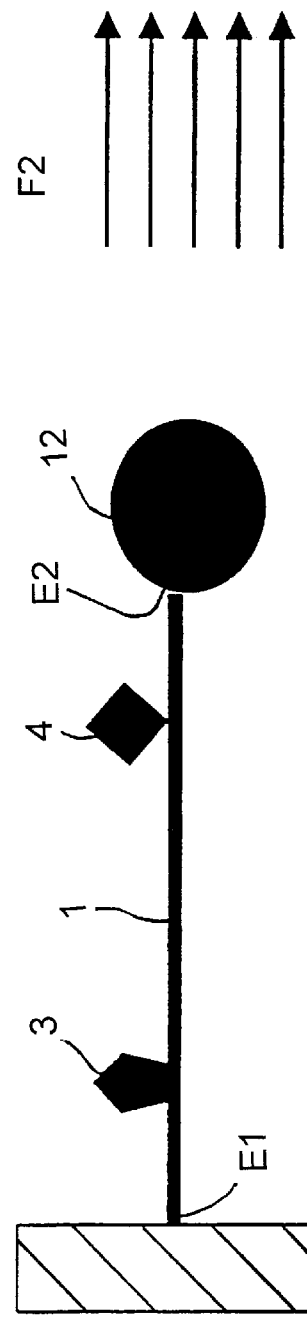

AGENT AND METHOD FOR DETECTING CHEMICAL SUBSTANCES

CROSS-REFERENCE TO RELATED APPLICATIONS

This application is a National Stage application under 35 U.S.C. §371 and claims benefit under 35 U.S.C. §119(a) of International Application No. PCT/DE99/00558 having an International Filing Date of Mar. 2, 1999, which claims benefit of DE 198 08 884.1 filed on Mar. 3, 1998.

The invention relates to an agent and a procedure for the detection of chemical substances and physical properties.

U.S. Pat. No. 5,607,834 discloses the use of a primer having a hairpin loop for the detection of a nucleotide sequence. In this procedure, a first and a second fluorophoric molecule are provided on the opposite loop sections of the hairpin loop. The fluorophoric molecules are designed here such that the fluorescence is extinguished by the radiation-free energy transfer. If the primer, however, is hybridized with a complementary opposite strand, the hairpin loop is opened. The spatial relationship between the first and the second fluorophoric molecule, which extinguishes fluorescence, is altered. Fluorescence is thus observable.—This procedure is only suitable for the detection of nucleotide sequences.

David J. Holme and Hazel Peck: Analytical biochemistry, Longnamm [sic], London and New York, 1983, pages 243–244 generally disclose the use of fluroimmonoassays [sic] for the detection of antigens.

It is the object of the present invention to specify an agent and a procedure which are universally suitable for the detection of chemical substances and physical properties.

According to the invention, an agent for the detection of chemical substances or physical properties is provided, having a first polynucleotide or peptide sequence having a first fluorophoric group, whose first end is bonded to a solid phase and a second polynucleotide or peptide sequence having a second fluorophoric group, whose second end has a group which is bondable or addable to the chemical substance to be detected or a group which is sensitive to the physical substance to be detected, the first polynucleotide or peptide sequence being addable to the second polynucleotide or peptide sequence such that a spatial relationship making possible an interaction between the first and the second fluorophoric molecule is producible, and during addition of the chemical substance to the group and/or action of an external force on the group the spatial relationship being terminatable and thus a fluorescence reaction is producible.

The agent is universally suitable for the detection of chemical substances and physical properties. For investigating the question of whether a certain chemical substance is contained in a solution, the agent is brought into contact with the solution. If the chemical substance is contained in the solution, it adds to the group. By the action of an external force directed away from the solid phase, e.g. of a centrifugal force, the spatial relationship between the first and the second fluorophoric group is altered. A fluorescence reaction is observable. This can be the extinguishing of a fluorescence formed in the presence of the spatial relationship. The fluorescence reactions are essentially based here on the so-called Förster effect.

To achieve the object, a procedure for the detection of chemical substances or physical properties is additionally provided, having a first polynucleotide or peptide sequence having a first fluorophoric group, whose first end is bonded to a solid phase and a second polynucleotide or peptide sequence having a second fluorophoric group, whose second end has a group which is bondable or addable to the chemical substance to be detected or a group which is sensitive to the physical property to be detected, the first polynucleotide or peptide sequence being addable to the second polynucleotide or peptide sequence such that a spatial relationship making possible an interaction between the first and the second fluorophoric molecule is formed, and during addition of the chemical substance to the group and/or action of an external force on the group the spatial relationship being terminated and thus a fluorescence reaction being produced.

The procedure is universally suitable for the detection of chemical substances and physical properties, such as, for example, the presence of a magnetic field. For this, for example, a magnetic chemical substance can be coupled to the group or a magnetic group can be provided. On applying a magnetic field which pulls the chemical substance or group away from the solid phase, the spatial relationship between the first and the second fluorophoric molecule is terminated. A fluorescence reaction is observable which indicates the presence of a magnetic field. The procedure according to the invention is moreover more rapid than conventional procedures for the detection of chemical substances, such as the ELISA procedure, because time-consuming conversion of a color-imparting substance is not necessary for the detection and because the washing steps for the removal of unbound antibodies are unnecessary.

According to one embodiment, the first and the second polynucleotide or peptide sequence are linked to give a molecule. In this case, the spatial relationship can be designed in the form of a secondary structure, in particular as a hairpin loop, helix or pleated sheet structure. Advantageously, the first fluorophoric molecule is bonded to a first loop section and the second fluorophoric molecule is bonded oppositely to a second loop section of the hairpin loop at a distance making possible an interaction.

The solid phase can be a, preferably electrically conductive, plastic. This expediently contains a polycarbonate, trimethylthiophene, thiophene, triaminobenzene and/or a polycarbene.

The polynucleotide sequence can be a deoxyribinucleic acid [sic] (DNA), a phospothionate nucleic acid [sic] (PTO) or a peptide nucleic acid (PNA). Instead of this, however, a peptide or a protein can also be used. The fluorescence reaction can be the production or the extinguishing of fluorescence.

Figure 6:
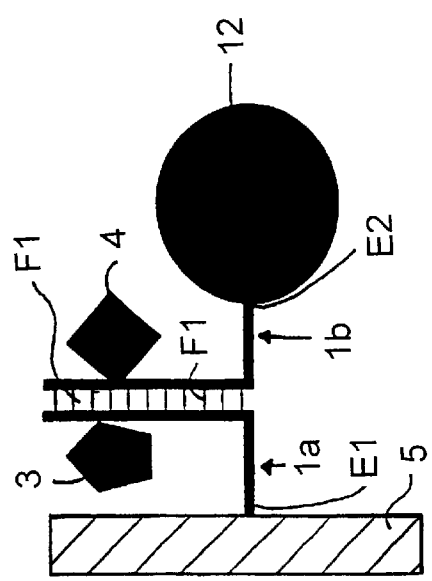
Figure 7:
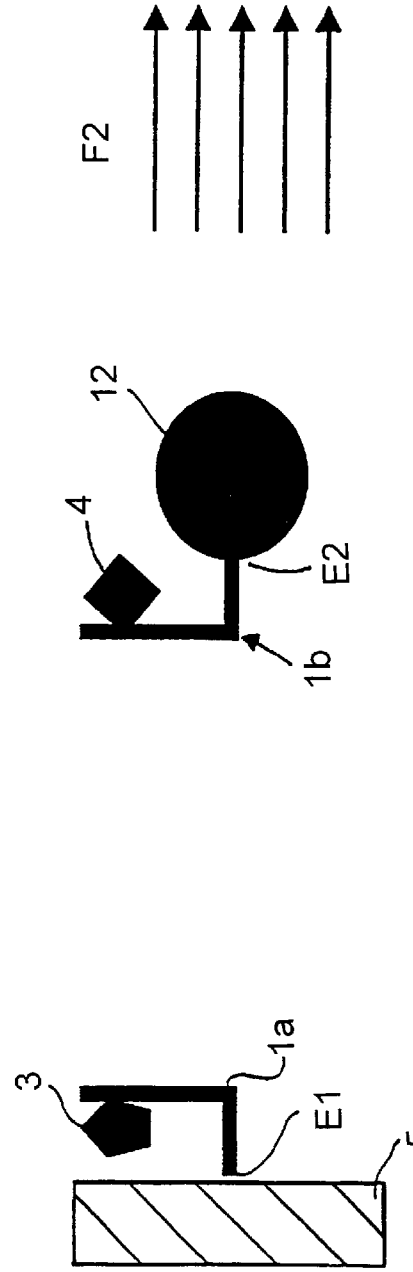

Exemplary embodiments of the agent and procedure are illustrated in more detail below with the aid of the drawing. In this drawing, FIG. 1 shows a schematic representation of the agent, FIG. 2 shows a schematic view according to FIG. 1, with an antigen bonded thereto and FIG. 3 shows a schematic view according to FIG. 2, the secondary structure being abolished, FIG. 4 shows a schematic representation of a second agent in the first state, FIG. 5 shows a schematic representation according to FIG. 4, the second agent being in the second state, FIG. 6 shows a schematic representation of a third agent in the first state and FIG. 7 shows a schematic representation according to FIG. 6, the third agent being in the second state.

In FIG. 1, the agent is shown schematically. A DNA 1 has a hairpin loop 2 having a first loop section 2a and a corresponding second opposite loop section 2b. To the first loop section 2a is bound a first fluorophoric group 3 and to the second loop section 2b a quencher 4. An interaction exists between the first fluorophoric group 3 and the quencher 4, which extinguishes fluorescence or specifically alters the wavelength of the emitted light. Instead of the quencher 4, a second fluorophoric group can also be provided. This can be a donor group. In this case, the first fluorophoric group consists of an acceptor group. Suitable donor/acceptor compounds are shown in the following table:

| Donor | Acceptor |
| --- | --- |
| Fluorescein | Fluorescein |
| 6-Carboxyfluorescein | 6-Carboxymethylrhodamine |
| Fluorescein | Tetramethylrhodamine |
| IAEDANS (= 5-((((2-iodoacyl)-amino)ethyl)amino)naphthalene-1-sulonic acid [sic] | Fluorescein |
| EDANS (= 5-((2-aminomethyl)-amino)naphthalene-1-sulfonic acid | DABCYL (4-dimethylaminoazo-benzene-4'-sulfoyl chloride [sic] |
| BODIPY FL | BODIPY FL |

A first end E1 of the DNA 1 is bonded to a solid phase 5, e.g. a polycarbonate. To a second end E2 of the DNA 1 is bonded an antibody 6, e.g. a CD4 antibody.

FIG. 2 shows the agent represented in FIG. 1, an antigen 7 to be detected, e.g. a CD4 antigen, being bonded to the antibody 6. A substance 8 is formed from a further group 9 addable or bondable to the antigen 7, e.g. a CD4 antibody, and a superparamagnetic particle 10. Superparamagnetic particles which can be used are magnetic beads, such as are supplied by the companies MILTENY or DYNATECH. Such magnetic beads can be coupled to a CD4 antibody by means of biotin for the formation of the substance 8. Instead of the superparamagnetic particle 10, a superparamagnetic group can also be used. The further group 9 is likewise bonded to the antigen 7 to be detected.

FIG. 3 shows the agent shown in FIG. 2 with added antigen 7 and a substance 8 coupled thereto. The hairpin loop 2 is abolished here. The acceptor group 3 and the quencher 4 are removed from one another to such an extent that an interaction no longer exists between them. A magnet is designated by the reference symbol The function of the agent is as follows:

A sample comprising the antigen 7 to be detected is added to the substance 8. The further group 9 of the substance 8 bonds to the antigen 7. The agent according to FIG. 1 is then brought into contact with the sample. The antigen 7 now bonds (with substance 8 coupled thereto) to the group 6. Subsequently, the magnet 11 is brought into the vicinity of the sample. The magnetic field is designed such that the superparamagnetic particles 10 are moved away from the solid phase 1. By means of the force acting thereby on the DNA 1, the hairpin loop 2 is abolished. The DNA 1 forms an elongated molecule. The interaction between the formerly opposite first fluorophoric group 3 and the quencher 4 no longer exists. On excitation of the first fluorophoric group 3, a fluorescence is now observable. The fluorescence reaction serves for the detection of the antigen 7.—For the detection, a donor/acceptor pair can also be used with which, on existence of the interaction, an increased fluorescence and, on abolishment of the interaction, a weakened fluorescence, is brought about.

The agent can now be removed from the sample. At the same time, the antigen 7 to be detected is removed from the sample therewith.

As a result of the fluorescence signal brought about in the presence of the antigen 7 to be detected, the agent can automatically be removed from the sample by means of a robot and for carrying out further process steps transferred to a device intended therefor.

In FIG. 4, a DNA or PNA 1 has a hairpin loop 2 having a first loop section 2a and a second loop section 2b complementary thereto. To the first loop section 2a is bonded a first fluorophoric group 3 and to the second loop section 2b a second fluorophoric group 4. The fluorophoric groups 3, 4 have a spatial separation which, on appropriate excitation, allows a fluorescence energy transfer. The fluorophoric groups 3, 4 can be a donor/acceptor pair or a donor/quencher pair. In this case, both the first fluorophoric group 3 and the second fluorophoric group 4 can have the donor or acceptor function.

The hairpin loop 2 is held together by a first force F1. The DNA 1 is bonded to the solid phase 5 by one end E1. This can be polysterol or polycarbonate. At one end of the DNA 1, biotin can be provided which reacts with a streptavidin coating provided there for bonding to the solid phase.

At the second end E2 of the DNA 1 is bonded a group 12. This can be an antibody, an antigen, a receptor or a ligand. If the detection of physical properties is to be carried out, the group can also be a magnetic group 12 or an electrically charged group.

In FIG. 5, the agent according to FIG. 4 is shown in the second state. A second force F2 acts on the magnetic group 12. This is a magnetic force. The second force F2 is greater than the first force F1.

On application of the second force F2, the DNA 1 is extended. The hairpin loop 2 is destroyed. The spatial relationship between the first fluorophoric group 3 and the second fluorophoric group 4 is terminated. A fluorescence energy transfer is no longer possible. The fluorophoric properties of the first fluorophoric group 3 and the second fluorophoric group 4 alter. On the basis of the alteration of the fluorophoric properties, a detection of a presence of a magnetic field is possible.

In FIGS. 6 and 7, a third agent for the detection of chemical substances or physical properties is shown. Here, to the solid phase 5 is bonded a first DNA 1a which carries the first fluorophoric group 3. The first DNA 1a is complementary sectionwise to a second DNA 1b, to whose second end is bonded the magnetic group 12. The second DNA 1b carries a quencher 4.

The first DNA 1a and the second DNA 1b are designed such that on arrangement of their complementary sequence sections next to one another, the first fluorophoric group 3 and the quencher 4 can enter into a spatial relationship which makes possible a fluorescence energy transfer.

On application of a magnetic field, a force F2 directed away from the solid phase 5 is exerted on the magnetic group 12. The second force F2 is greater than the first force F1, with which the first DNA 1a and the second DNA 2a are held together in the first state shown in FIG. 6. Under the action of the second force F2, the second DNA 1b detaches from the first DNA 1a. The spatial relationship between the first fluorophoric group 3 and the quencher 4 is eliminated.

A fluorescence energy transfer is no longer possible. Owing to this, a fluorescence reaction is caused which indicates the presence of a magnetic field.

EXAMPLE

Production of a Magnetic Field Sensor

1. Synthesis of a DNA Hybrid of a [Lacuna] Having a Fluorescence-active Group

Two oligonucleotides of a length of 40 bases are synthesized. The sequences of the oligonucleotides are complementary to one another. The melting point of the oligonucleotides is about 70° C. A first oligonucleotide carries an amino linker at the 3' end and a fluorescein group at the 5' end. A second oligonucleotide carries a Dabcyl group at the 3' end and a biotin molecule at the 5' end. The oligonucleotides supplied by the manufacturer (TibMol Biol, Berlin) in the freeze-dried state are dissolved in sterile water in a concentration of 100 mM. 100 µl each of the solutions are brought together in a 500 µl reaction vessel and heated at 95° C. for 5 min. The sample is then cooled to 68° C. (2 min below the melting point of the oligonucleotides) for 15 min and then stored at 4° C.

2. Coupling of the DNA Hybrid to a Maleic Anhydride-activated Plastic Surface

100 µl of the synthesized DNA hybrid is added to each cavity of a maleic anhydride-activated microtiter plate (Pierce, KMF, Berg.-Gladbach). The DNA is incubated with the surface overnight with shaking at 4° C. The solution is then removed from the surface and it is washed 3 times with 150 µl of sterile water each time. For the saturation of activated bonding sites present, the surface is incubated 3 times at room temperature with 150 µl of sterile 10 mM TrisCl, 1 mM EDTA for 5 min. The surface is stored in sterile 100 µl [sic] mM TrisCl, 1 mM EDTA ph [sic] 8 at 4° C.

3. Bonding to Superparamagnetic Particles

Streptavidin-coated superparamagnetic particles of the [lacuna] (Dynal, Hamburg) are suspended 1:1 (v/v) in 10 mM TrisCl, 1 mM EDTA ph [sic] 8. About 5 µl of particle suspension are in each case added to a coated well of the microtiter plate. The particles are distributed on the surface by gentle tapping of the microtiter plate. The suspension is incubated at room temperature for 15 min.

4. Detection of a Magnetic Field by Means of an FET-based Sensor

The fluorescence of the microtiter plate is observed in a microtiter plate reader and in a fluorescence microscope. As excitation energy, the wavelength for the excitation of the fluorescein is in this case measured at 491 nm and the emission at 515 nm. A permanent magnet is introduced into the solution at defined distances from the bottom of the microtiter plate and removed again after 20 sec. The increase in the fluorescence indicates the presence of a magnetic field. The control used is a microtiter plate which carries an attached DNA hybrid which has been identically treated but carries no biotin.

REFERENCE SYMBOL LIST

1 DNA
1a First DNA
1b Second DNA
2 Hairpin loop
2a First loop section
2b Second loop section
3 First fluorophoric group
4 Quencher
5 Solid phase
6 First antibody
7 Antigen
8 Substance
9 Second antibody
10 Superparamagnetic particle
11 Permanent magnet
12 Magnetic group
E1 First end
E2 Second end
F1 First force
F2 Second force

What is claimed is:

1. A method for the detection of chemical substances, comprising:

providing an agent comprising a first polynucleotide or peptide sequence having a first fluorophoric molecule, wherein first end of said first polynucleotide or peptide sequence is bonded to a solid phase, and a second polynucleotide or peptide sequence having a second fluorophoric molecule, wherein a second end of said second polynucleotide or peptide sequence has a group which is sensitive to the chemical substance to be detected, said chemical substance comprising a physical property sensitive to an external force, the first polynucleotide or peptide sequence being hybridizable to the second polynucleotide or peptide sequence such that a spatial relationship making possible an interaction between the first and the second fluorophoric molecule is producible, and the spatial relationship being terminatable and thus a fluorescence reaction being producible upon addition of the chemical substance to the group and action of an external force;

contacting the agent with the chemical substance to be detected;

applying the external force; and detecting the presence or absence of the fluorescence reaction.

2. The method according to claim 1, the first and the second polynucleotide or peptide sequence being linked to give a molecule.

3. The method according to claim 1, the spatial relationship being designed in the form of a secondary structure.

4. The method according to claim 3, the secondary structure being a hairpin loop, a helix or a pleated sheet.

5. The method according to claim 4, the first fluorophoric molecule being bonded to a first loop section and the second fluorophoric molecule being bonded oppositely to a second loop section of the hairpin loop at a distance making possible an interaction.

6. The method according to claim 1, the solid phase being plastic.

7. The method according to claim 6, the plastic comprising polycarbonate, trimethylthiophene, thiophene, triaminobenzene or polycarbene.

8. The method according to claim 6, the plastic being electrically conductive.

9. The method according to claim 1, the first fluorophoric molecule being an acceptor molecule and the second fluorophoric molecule being a donor molecule.

10. The method according to claim 9, the acceptor molecule being 6-carboxytetramethylrhodamine, tetramethylrhodamine, fluorescein, DABCYL or Bodipy Fl.

11. The method according to claim 9, the donor molecule being 6-carboxyfluorescene, fluorescein, IADEANS, EDANS or Bodipy Fl.

12. The method according to claim 1, the first fluorophoric molecule being replaced by a quencher.

13. The method according to claim 1, the polynucleotide sequence being DNA, PTO or PNA.

14. The method according to claim 1, the group being an antibody, a receptor, an antigen, or a ligand.

15. The method according to claim 14, wherein a substance which contains a recognizing group suitable for recognizing the chemical substance and having a superparamagnetic particle bonded thereto is added to the sample containing the chemical substance.

16. The method according to claim 15, the chemical substance to be detected being bonded to the group which is sensitive to the chemical substance and to the recognizing group.

17. The method according to claim 16, a magnetic field being applied such that the superparamagnetic particle moves away from the solid phase and the secondary structure is abolished or altered thereby.

18. The method according to claim 1, the fluorescence being detected by means of a fluorometer connected to a data processing device.

19. The method according to claim 18, the concentration of the chemical substance to be detected being determined from the temporal alteration of the fluorescence intensity.

20. An agent for the detection of chemical substances, having a first polynucleotide or peptide sequence having a first fluorophoric molecule, wherein a first end of said first polynucleotide or peptide sequence is bonded to a solid phase, and a second polynucleotide or peptide sequence having a second fluorophoric molecule, wherein a second end of said second polynucleotide or peptide sequence has a group which is sensitive to the chemical substance to be detected, said chemical substance comprising a physical property sensitive to an external force, the first polynucleotide or peptide sequence being hybridizable to the second polynucleotide or peptide sequence such that a spatial relationship making possible an interaction between the first and the second fluorophoric molecule is producible, and the spatial relationship being terminatable and thus a fluorescence reaction being producible in the presence of the chemical substance and action of said external force, wherein the spatial relationship is designed in the form of a secondary structure, wherein the secondary structure is a hairpin loop, a helix or a pleated sheet.

21. An agent for the detection of chemical substances, having a first polynucleotide or peptide sequence having a first fluorophoric molecule, wherein a first end of said first polynucleotide or peptide sequence is bonded to a solid phase, and a second polynucleotide or peptide sequence having a second fluorophoric molecule, wherein a second end of said second polynucleotide or peptide sequence has a group which is sensitive to the chemical substance to be detected, said chemical substance comprising a physical property sensitive to an external force, the first polynucleotide or peptide sequence being hybridizable to the second polynucleotide or peptide sequence such that a spatial relationship making possible an interaction between the first and the second fluorophoric molecule is producible, and the spatial relationship being terminatable and thus a fluorescence reaction being producible in the presence of the chemical substance and action of said external force, wherein the solid phase is plastic, wherein the plastic is electrically conductive.

* * * * *